(12) United States Patent
Bergemann et al.

(10) Patent No.: US 6,758,891 B2
(45) Date of Patent: Jul. 6, 2004

(54) CARBON-CONTAINING MATERIAL

(75) Inventors: Klaus Bergemann, Kerpen-Sindorf (DE); Egon Fanghaenel, Halle (DE); Bernd Knackfuss, Strelln (DE); Thomas Luethge, Hanau (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/260,402

(22) Filed: Oct. 1, 2002

(65) Prior Publication Data

US 2003/0101901 A1 Jun. 5, 2003

Related U.S. Application Data

(60) Provisional application No. 60/328,817, filed on Oct. 15, 2001.

(30) Foreign Application Priority Data

Oct. 9, 2001 (DE) ......................... 101 49 805

(51) Int. Cl.$^7$ ............................................. C09D 11/00
(52) U.S. Cl. ...................... 106/31.8; 106/31.9; 106/472
(58) Field of Search .............................. 106/31.8, 31.9, 106/472

(56) References Cited

U.S. PATENT DOCUMENTS 4,407,882 A * 10/1983 Hauser et al. .............. 428/159
5,296,033 A * 3/1994 Dietz et al. .................. 106/412
5,685,901 A * 11/1997 Bugnon ....................... 106/494

FOREIGN PATENT DOCUMENTS

| EP | 1 134 261 | 9/2001 |
| EP | 1 136 526 | 9/2001 |
| WO | WO 96/18690 | 6/1996 |

* cited by examiner

*Primary Examiner*—Mark L. Bell
*Assistant Examiner*—Veronica F. Faison
(74) *Attorney, Agent, or Firm*—Oblon, Spivak, McClelland, Maier & Neustadt, P.C.

(57) ABSTRACT

A carbon-containing material with organic groups, which is obtainable by reaction of the carbon-containing material with organic compounds of the general formula 1

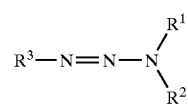

(1)

A process for preparing the carbon-containing material according to the invention is also described. The carbon-containing materials according to the invention can be used as fillers, reinforcing fillers, UV stabilizers, conductivity carbon blacks or pigments.

17 Claims, No Drawings

CARBON-CONTAINING MATERIAL

DETAILED DESCRIPTION OF THE INVENTION

FIELD OF THE INVENTION

The present invention provides a carbon-containing material, a process for its preparation, and its use.

DESCRIPTION OF THE BACKGROUND

EP 0569503 discloses a process for the surface modification of carbon-containing materials with aromatic groups by the electrochemical reduction of a diazonium salt.

Furthermore, it is known that carbon black can be provided with organic groups by linking the organic groups to the carbon-containing material via reaction with diazonium salts that are obtained by diazotization (WO 96/18690) or bonding the organic groups to the carbon black by reactions with radical producers (Ohkita K., Tsubokawa N., Saitob E., Carbon 16 (1978) 41), DE 10012784.3) or via cycloaddition reactions (DE 10012783.5, JP 11315220 A).

Known processes have the following disadvantages:

Apart from toxic and flame-supporting sodium nitrite, the non-ionic organic nitrites which can also be used for diazotisation are toxic and readily inflammable. Residues of nitrites (gegenions, alkyl groups) remain, unbonded, as impurities in the carbon black.

The use of a nitrite in acid medium is required in order to perform a diazotisation reaction. Toxic nitrogen oxides may thus also be produced.

Radical producers are thermally or photochemically labile, potentially explosive and may lead to chain reactions which are difficult to control.

The synthesis and purification of the corresponding precursors of radical producers sometimes proceeds via toxic substances or those which cause a nuisance due to odor.

The elimination of nitrogen which takes place during cyclisation reactions with nitrogen heterocyclic compounds can lead to sudden, explosion-like increases in volume or rises in pressure which makes reaction management substantially more difficult.

SUMMARY OF THE INVENTION

It is an object of the invention to provide a carbon-containing material with organic groups, wherein modification of the carbon-containing material can be varied in such a way that the groups are located directly on the surface of the carbon-containing material and/or may also be displaced well away from the surface of the carbon-containing material, modification of the carbon-containing material proceeds without the need for preliminary reactions such as activation by starters, reactions with the modification agents used in accordance with the invention proceed thermally and catalysts (for example Lewis acids) are not required, due to the chemical properties of the modification agents used in accordance with the invention, no problematic side reactions or difficult to control chain reactions can take place, the resulting carbon-containing material is not contaminated with acids, salts and the like so no purification of the carbon-containing material is required, the carbon-containing material does not have to be dried with the consumption of large amounts of energy, no toxic waste gases are produced during modification, and/or no solvents, or only small amounts of readily removable solvents, are required.

The invention provides a carbon-containing material with organic groups, wherein this is obtainable by reaction of the carbon-containing material with organic compounds of the general formula 1:

$$R^3-N=N-N\begin{matrix}R^1\\R^2\end{matrix} \quad (1)$$

where $R^1$, $R^2$ and $R^3$ are identical or different and comprise H or alkyl or aryl groups with acceptor or donor substituents and/or hydrophilic or hydrophobic groups or $R^1$ and $R^3$ form a cyclic system with the three nitrogen atoms and $R^2$ comprises H or alkyl or aryl groups with acceptor or donor substituents and/or hydrophilic or hydrophobic groups.

The present invention also provides a composition, comprising the carbon-containing material described above and at least one member selected from the group consisting of rubber, plastics, printing inks, inks, inkjet inks, lacquers, toners and colorants, bitumen, concrete, other constructional materials, and paper.

The present invention also provides a method of making the composition described above, comprising incorporating the carbon-containing material into a member selected from the group consisting of rubber, plastics, printing inks, inks, inkjet inks, lacquers, toners and colorants, bitumen, concrete, other constructional materials, and paper.

The present invention also relates to a dispersion, which contains the carbon-containing material with organic groups described above.

The present invention also provides an ink, lacquer, toner, or colorant contain the dispersion described above.

The present invention also provide a method of making the ink, lacquer, toner or colorant described above, comprising incorporating the dispersion in to the ink, lacquer, toner, or colorant.

The present invention also provides compound represented by the formula 2 or 3:

(2)

[Structure: naphthalene with SO₃Y and YO₃S substituents, connected via -N=N- to a benzotriazole group]

-continued (3)

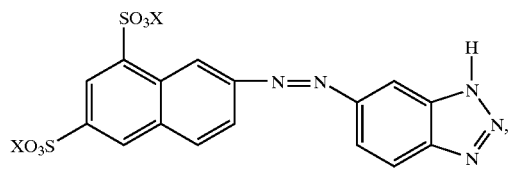

wherein

X is H, metal$^{n+}$, or N$^+$(R$^4$)$_4$,

Y is H, metal$^{n+}$, or N$^+$(R$^4$)$_4$, n is 1, 2, or 3, u is 1, 2, or 3, and R$^4$ is H or an alkyl or aryl group or a functionalized alkyl group or a functionalized aryl group.

A more complete appreciation of the invention and many of the attendant advantages thereof will be readily obtained as the same becomes better understood by reference to the following Figures in conjunction with the detailed description below.

DETAILED DESCRIPTION OF THE INVENTION

The cyclic system may contain nitrogen, carbon or other heteroatoms, for example sulfur or oxygen, and may be, for example, a triazole, tetrazole or pentazole.

The following may be used as triazole compounds:

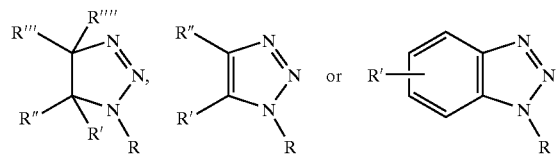

wherein R, R', R", R''', R'''' are identical or different and comprise H or alkyl or aryl groups with acceptor or donor substituents or parts of cyclic systems with acceptor or donor substituents and/or hydrophilic or hydrophobic groups.

The following may be used in particular as triazole compounds

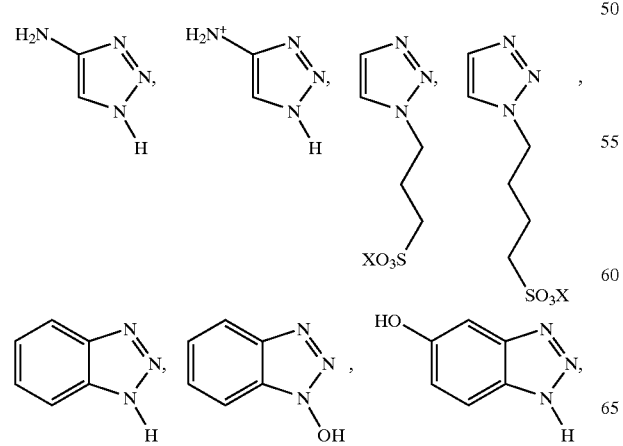

-continued

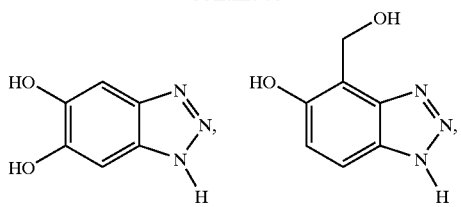

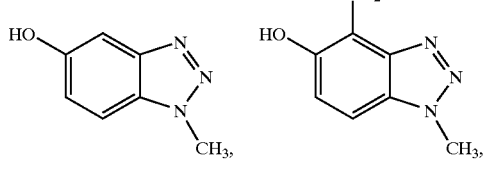

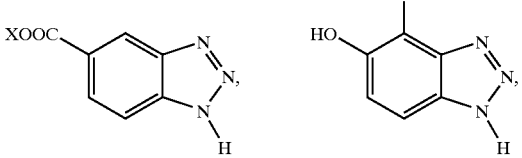

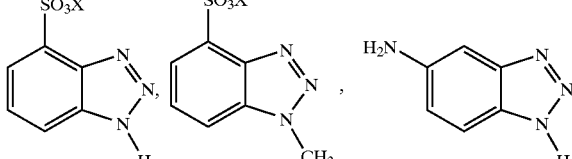

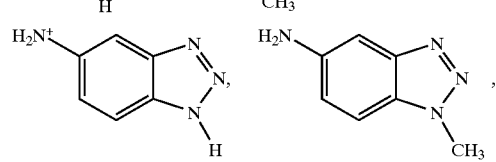

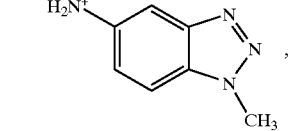

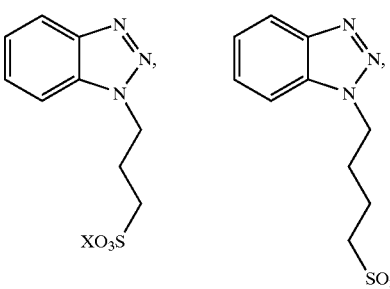

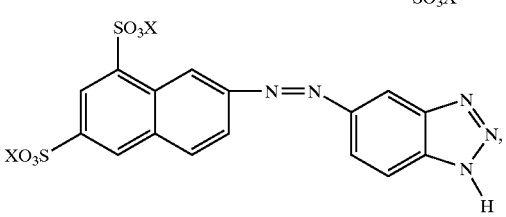

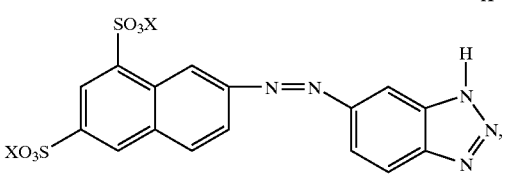

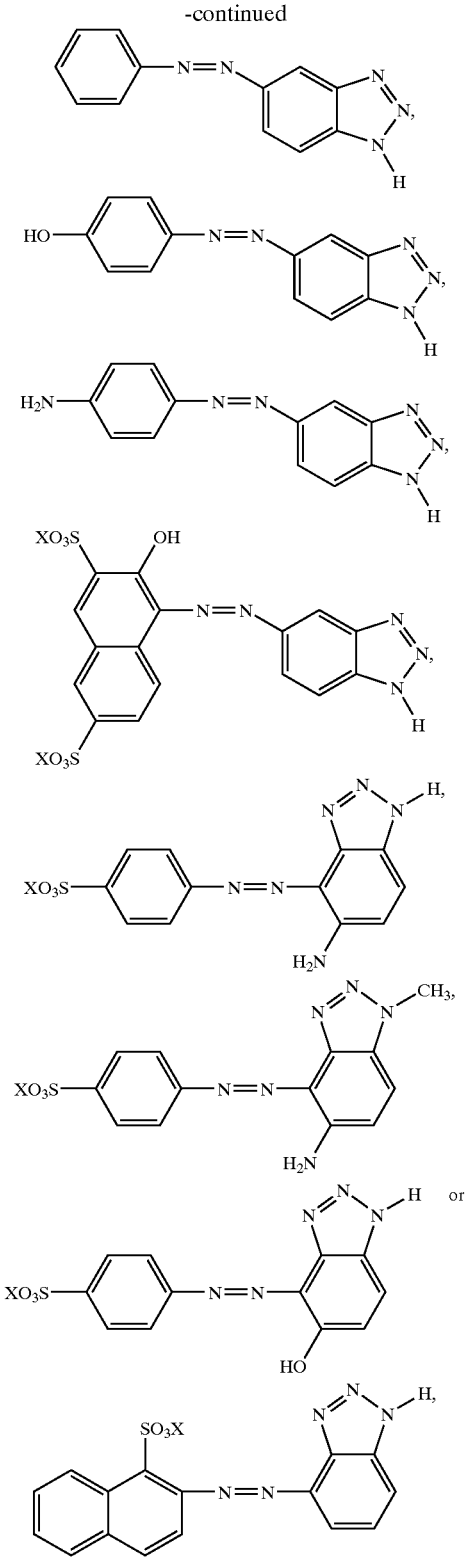

where X=H, metal $^{n+}$(n=1–3), $N^+(R^4)_4$,

Acceptor substituents may be —COOR$^4$, —CO—R$^4$, —CN, —SO$_2$R$^4$ or —SO$_2$OR$^4$ where R4=H or alkyl, aryl or functionalized alkyl or aryl groups such as, for example, ω-carboxyalkyl, HSO$_3$—C$_x$H$_y$—, H$_2$N—C$_x$H$_y$— or H$_2$—NSO$_2$C$_x$H$_y$— (x=1–20, y=1–45; preferably, x,y=1–5).

Donor substituents may be alkyl or aryl groups, OR$^5$ or N(R$^5$)$_2$ where R$^5$=H or alkyl, aryl or functionalized alkyl or aryl groups.

The organic groups R$^1$, R$^2$ and R$^3$ may be:

an aliphatic group including a cyclic organic group or an organic compound with an aliphatic and a cyclic section, substituted or unsubstituted, branched or unbranched, an aliphatic group containing, for example, groupings from alkanes, alkenes, alcohols, ethers, aldehydes, ketones, carboxylic acids, hydrocarbons, sulfonic acids or trialkylammonium, trialkylphosphonium or dialkylsulonium, a cyclic compound, for example alicyclic hydrocarbons such as for example cycloalkyl or cycloalkenyl, heterocyclic compounds, such as for example pyrrolidinyl, pyrrolinyl, piperidinyl or morpholinyl, aryl groups such as for example, phenyl, naphthyl or anthracenyl and heteroaryl groups such as for example imidazolyl, pyrazolyl, pyridinyl, thienyl, thiazolyl, furyl or indolyl, substituted by other functional groups, a chromophoric group or a dye, suitable reactive compounds, such as for example triarylammonium, triarylphosphonium, diarylsulfonium and aryliodonium.

Compounds of the general formula 1 where R$^1$, R$^2$ or R$^3$=H may be functionalized later by alkylation or arylation reactions. In addition, the primary groups introduced may be modified by further secondary reactions.

The substituents in the organic compounds of the general formula 1 can then be tailored to the potential area of application because the principle of reaction permits, for example, the introduction of hydrophilic, or else of lipophilic substituents. The substituents may also be ionic, polymeric or able to react in further, reactions. Various properties of the carbon-containing materials which are of use in the ultimate application can be altered in a targeted manner via the substituents. Thus, for example, the hydrophilicity of the carbon-containing material can be increased so much that the carbon-containing material forms dispersions which are stable in aqueous media without the use of a wetting agent.

Carbon-containing materials which can be used are carbon black, graphite powder, graphite fibres, carbon fibres, carbon fibrils, carbon nanotubes, carbon fabrics, glass-like carbon products and active carbon.

Carbon blacks which can be used are any known carbon blacks such as, for example, furnace black, gas black, channel black, flame black, thermal black, acetylene black, plasma black, inversion blacks, disclosed in DE 195 21 565, incorporated herein by reference, Si-containing blacks, disclosed in WO 98/45361 or DE 19613796, both incorporated herein by reference, or metal-containing blacks, disclosed in WO 98142778, incorporated herein by reference, electric arc black and blacks which are the secondary products of chemical production processes. The carbon black can be activated in preliminary reactions. Carbon blacks which are used as reinforcing fillers in rubber mixtures can be used. Colorant carbon blacks can be used. Other carbon blacks may be: conductivity black, blacks used for UV stabilisation, blacks used as fillers in systems other than rubber such as, for example, bitumen, plastics, carbon blacks used as reducing agents in metallurgy.

The invention also provides a process for preparing carbon-containing materials according to the invention, wherein carbon-containing material is reacted with organic compounds of the general formula 1.

The organic compound can be applied to the carbon-containing material by blending or premixture or by spraying. The organic compound can be applied as a powder, as a molten substance or as a solution. Particularly advantageously, the organic compound can be applied during preparation of the carbon-containing material, wherein addition of the organic compound preferably takes place at a location which has the requisite temperature. The reaction to modify the carbon-containing material is preferably a solvent-free reaction, but may also take place in a solvent, preferably a highly volatile organic solvent. The reaction to modify the carbon-containing material can be performed at temperatures of −80° to 250° C., preferably 80° to 180° C. The energy input can be achieved by means of mechanical energy, vibrational energy, for example ultrasound, or radiated energy, for example microwave radiation, heat radiation, light radiation, X-ray radiation and electron radiation.

The carbon-containing materials with organic groups in accordance with the invention can be used, for example, as fillers, reinforcing fillers, UV stabilizers, conductivity carbon black or pigments in rubber, plastics, printing inks, inks, inkjet inks, lacquers, toners and colorants, bitumen, concrete and other constructional materials or paper. Furthermore, the carbon-containing materials according to the invention can be used as reducing agents in metallurgy.

The invention also provides an organic compound for preparing carbon-containing materials with organic groups in accordance with the invention, wherein this corresponds to the general formula 2 or 3:

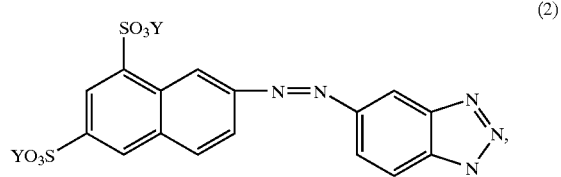

(2)

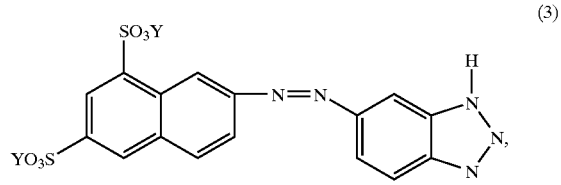

(3)

wherein Y represents H, metal$^{u+}$(u=1–3) or N$^+$(R$^4$)$_4$,

The invention also provides a dispersion, wherein it contains carbon-containing material with organic groups in accordance with the invention.

The dispersion according to the invention can be used in printing inks, inks, lacquers, toners and colorants.

Carbon-containing materials in accordance with the invention have the advantage that
- polar modified carbon-containing materials (for example those with —SO$_3^-$ substituents) are easier to disperse in polar systems, above all in water,
- non-polar modified carbon-containing materials (for example with alkyl groups) are easier to disperse in non-polar systems such as, for example, oils,
- suitably modified carbon-containing materials with polar or sterically hindered groups are electrostatically or sterically stabilized in systems and no other auxiliary substances, such as for example wetting agents, are required for stabilisation purposes,
- carbon-containing materials modified by the process according to the invention are better stabilized in dispersions and thus have better coloristic properties such as depth of color and blueness,
- carbon-containing materials with bonded colorants have modified shades of color,
- furthermore, carbon-containing materials with reactive substituents for coupling and cross-linking can be used in systems (for example rubber),
- reactively modified carbon-containing materials facilitate linkage of the carbon-containing material to the polymer,
- carbon-containing materials which contain very small amounts of secondary products, salts, acids and moisture can be prepared.

EXAMPLES

Having generally described this invention, a further understanding can be obtained by reference to certain specific examples which are provided herein for purposes of illustration only and are not intended to be limiting unless otherwise specified.

FW1 and Printex 35 are used as carbon blacks in the examples; however, modifications are not restricted to these types of carbon black. The carbon blacks mentioned are products of Degussa AG. Elemental analyses are determined using a Leco CHNS-932. A Varian Gemini 300 (δ-scale, internal standard type TMS) is used to record the $^1$H-NMR spectra (300 MHz). The dynamic and static surface tension are measured using a bubble tensiometer BP2 from Krüss; the viscosity is measured with a Physica US 200 (double slit measuring system) and the pH with a CG 837 pH meter.

Example 1

Synthesis and characterisation of the dipotassium salt of 7-[(1H-benzotriazol-5-yl)azo]-1,3-naphthalenedisulfonic acid, dipotassium salt

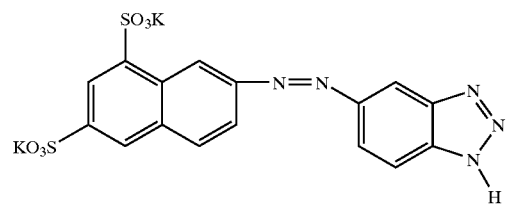

3 g of the monohydrated monopotassium salt of 2-naphthylamine-6,8-disulfonic acid and 1.5 g NaBF$_4$ are stirred into 30 ml water and dissolved by adding a little KOH. Then the amine is precipitated in a finely dispersed form using conc. HCl, the dispersion is cooled to 0° C. and a solution of 0.7 g NaNO$_2$ in 5 ml water is added slowly and dropwise. After completion of dropwise addition, the mixture is stirred for a further 20 minutes at 0° C. and then filtered under suction. The filter residue is added in portions to a solution of 1.2 g 1H-benzotriazole and 1 g KOH in 30 ml water cooled to 5–10° C. The solution is stirred for 30 minutes and the product is then precipitated with 400 ml acetone.

Molecular weight: 509 g/mol.
Yield: 95%.
Elemental analysis [%]: calculated: C-37.71; H-1.78; N-13.74; S-12.58. found: C-38.05; H-1.53; N-13.89; S-12.27;
$^1$H-NMR δ [ppm] (J [Hz]); DMSO$_{d6}$; 6.15 (s, 1H); 6.93 (d, 1H, J=9.9); 7.03 (d, 1H, J=10.2); 7.73 (s, 1H); 7.82 (d, 1H, J=9.0); 8.03 (d, 1H, J=9.0); 8.16 (s, 1H); 8.34 (s, 1H); 9.45 (s, 1H).

Modification of carbon black in the solid phase with the dipotassium salt of 1H-benzotriazol-5-azo-2'-naphthyl-6',8'-disulfonic acid 2 g of the dipotassium salt of 1H-benzotriazol-5-azo-2'-naphthyl-6',8'disulfonic acid are dissolved in 150 ml water, 10 g carbon black FW1 are added to the solution and then the solvent is distilled off under vacuum. Following this, the mixture is heated at 180° C. for 10 hours. The modified carbon black is washed with 300 ml water and then dried for eight hours at 100° C.

Example 2

Modification of Carbon Black in Water with the Dipotassium Salt of 1H-benzotriazol-5-azo-2'-naphthyl-6',8'-disulfonic Acid 2 g of the dipotassium salt of 1H-benzotriazol-5-azo-2'-naphthyl-6',8'-disulfonic acid are dissolved in 200 ml water. 10 g of carbon black FW 1 are added to the solution. Then the solution is boiled under reflux for twelve hours. After this, the carbon black is filtered under suction and the filter residue is washed with 400 ml water. The modified carbon black is dried for eight hours at 100° C.

Example 3

Modification of Carbon Black in the Solid Phase with 1H-Benzotriazole-1-butanesulfonic Acid, Sodium Salt

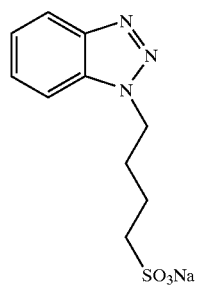

2 g of the sodium salt of ω-(1-benzotriazolyl)-butanesulfonic acid are dissolved in 250 ml water, 10 g carbon black Printex 35 are added to the solution and then the solvent is distilled off under vacuum. Following this, the mixture is heated at 180° C. for 6 hours. The modified carbon black is washed with 250 ml water and then dried for eight hours at 100° C.

Example 4

Modification of Carbon Black in Water with the Sodium Salt of ω-(1-benzotriazolyl)-butanesulfonic Acid 2 g of the sodium salt of ω-(1-benzotriazolyl)-butanesulfonic acid are suspended in 150 ml water. 10 g carbon black Printex 35 are added to the suspension. Then the mixture is boiled under reflux for 8 hours. Then the carbon black is filtered under suction and the filter residue is washed with 350 ml water. The modified carbon black is dried for eight hours at 100° C.

Example 5

Dispersion of Modified Carbon Black in Water 15 g of functionalized carbon black in accordance with example 1 are stirred into 85 ml water and then dispersed for 30 minutes at 5000 rpm using an Ultra Turrax. The dispersion obtained is stable without the further addition of a wetting agent.

Dynamic surface tension at 15 ms: 63 mN/m
Static surface tension at 3000 ms: 60 NmVm
pH: 7.5
Viscosity: 2.5 mPas Example 6

Dispersion of Modified Carbon Black in Water 15 g of functionalized carbon black in accordance with example 2 are stirred into 85 ml water and then dispersed for 30 minutes at 5000 rpm using an Ultra Turrax. The dispersion obtained is stable without the further addition of a wetting agent.

Dynamic surface tension at 15 ms: 59 mN/m
Static surface tension at 3000 ms: 55 Nm/m
pH: 7.3
Viscosity: 3.0 mPas Example 7

Dispersion of Modified Carbon Black in Water 15 g of functionalized carbon black in accordance with example 3 are stirred into 85 ml water and then dispersed for 30 minutes at 5000 rpm using an Ultra Turrax. The dispersion obtained is stable without the further addition of a wetting agent.

Dynamic surface tension at 15 ms: 65 mN/m
Static surface tension at 3000 ms: 61 Nm/m
pH: 7.8
Viscosity: 2.5 mPas Example 8

Dispersion of Modified Carbon Black in Water 15 g of functionalized carbon black in accordance with example 4 are stirred into 85 ml water and then dispersed for 30 minutes at 5000 rpm using an Ultra Turrax. The dispersion obtained is stable without the further addition of a wetting agent.

Dynamic surface tension at 15 ms: 62 mN/m
Static surface tension at 3000 ms: 59 Nm/m
pH: 1.7
Viscosity: 2.5 mPas Obviously, numerous modifications and variations of the present invention are possible in light of the teachings. It is therefore to be understood that within the scope of the appended claims, the invention may be practiced otherwise than as specifically described herein.

This application is based on German Patent Application Serial No. 101 49 805.5, filed on Oct. 9, 2001, incorporated herein by reference.

What is claimed is:

1. A carbon-containing material with organic groups, which is obtainable by a process, comprising:

reacting a carbon-containing material selected from the group consisting of carbon black, graphite powder, graphite fibers, carbon fibers, carbon fibrils, carbon nanotubes, carbon fabrics, glass-like carbon products and active carbon with an organic compound represented by formula 1:

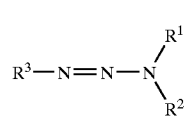

(1)

wherein

R$^1$, R$^2$ and R$^3$ are each, independently, H or an alkyl or aryl group with one or more acceptor or donor substituents and/or one or more hydrophilic or hydrophobic groups, or R$^1$ and R$^3$ form a cyclic group together with the three N atoms, and R$^2$ is H or an alkyl or aryl group with one or more acceptor or donor substituents and/or one or more hydrophilic or hydrophobic groups.

2. The carbon-containing material of claim 1, wherein the acceptor substituents are —COOR$^4$, —CO—R$^4$, —CN, —SO$_2$R$^4$, —SO$_2$OR$^4$, wherein R$^4$ is H or an alkyl or aryl group or a functionalized alkyl group or a functionalized aryl group.

3. The carbon-containing material of claim 1, wherein the donor substituents are alkyl or aryl groups, OR$^5$ or N(R$^5$)$_2$, wherein R$^5$ is H or an alkyl or aryl group or a functionalized alkyl group or a functionalized aryl group.

4. The carbon-containing material of claim 1, wherein the organic compound represented by formula 1 is

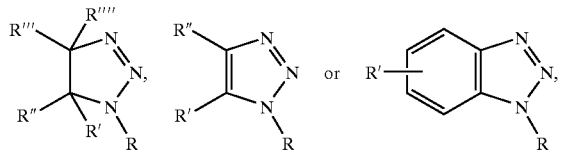

wherein R, R', R'', R''', R'''' are each, independently, H or an alkyl or aryl group with one or more acceptor or donor substituents or parts of a cyclic system with one or more acceptor or donor substituents and/or one or more hydrophilic or hydrophobic groups.

5. The carbon-containing material of claim 1, wherein the organic compound represented by formula 1 is

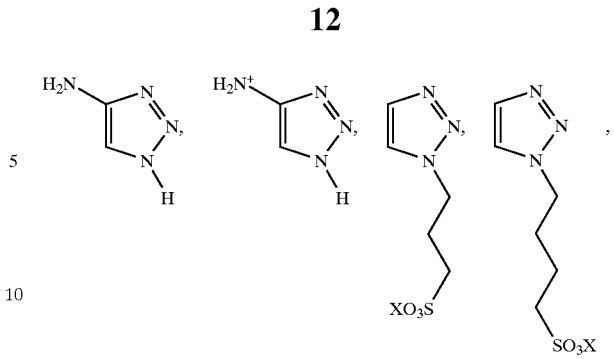

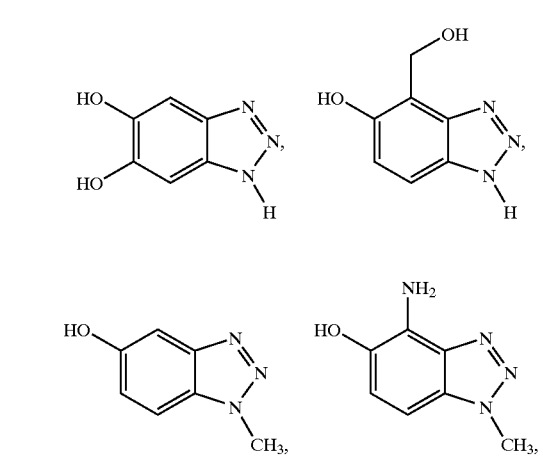

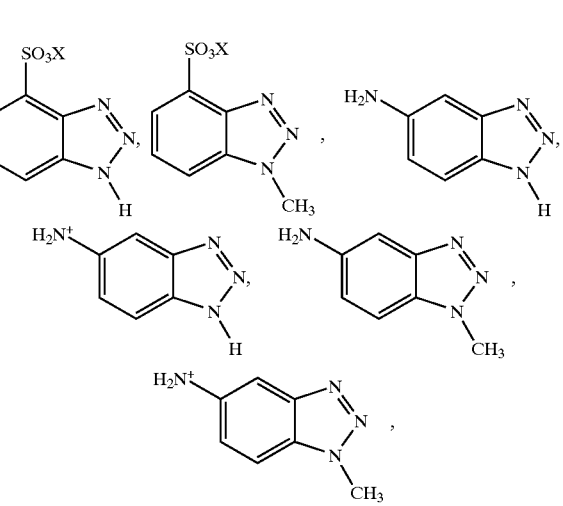

-continued

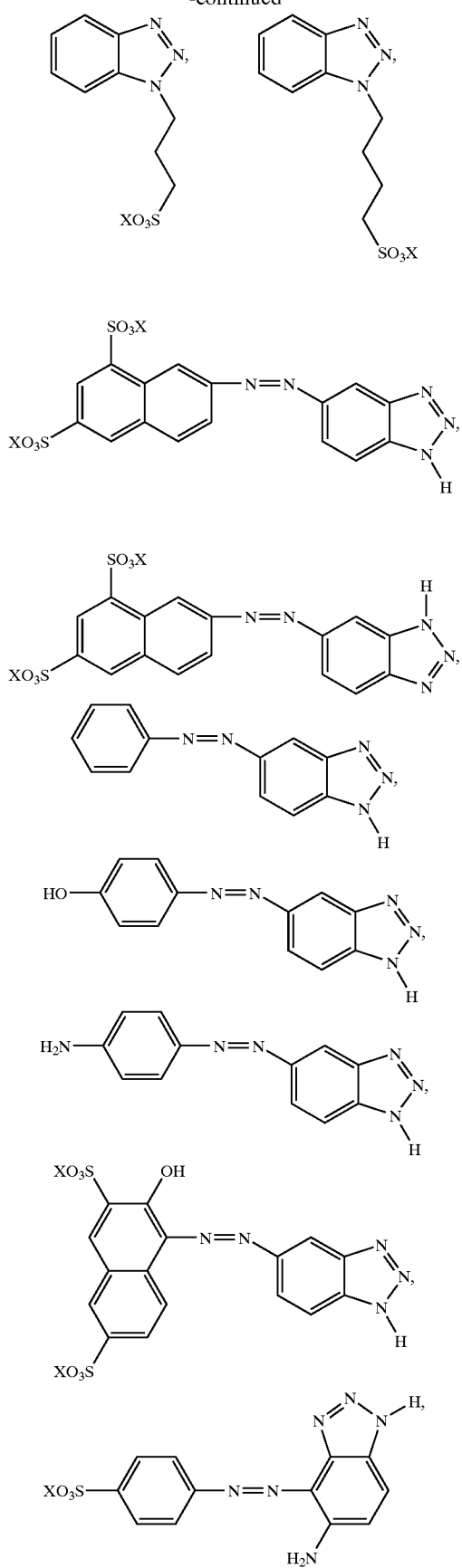

-continued

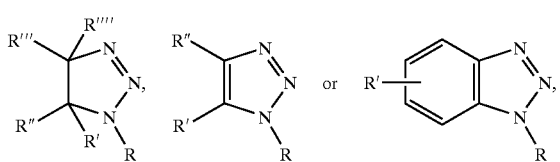

wherein
X is H, metal$^{n+}$, or $N^+(R^4)_4$,
n is 1, 2, or 3, and
$R^4$ is H or an alkyl or aryl group or a functionalized alkyl group or a functionalized aryl group.

6. A process for preparing a carbon-containing material of claim 1, comprising:

reacting the carbon-containing material as defined in claim 1 with the organic compound represented by formula 1.

7. The process of claim 6, wherein the acceptor substituents are —COOR$^4$, —CO—R$^4$, —CN, —SO$_2$R$^4$, or —SO$_2$OR$^4$, wherein R$^4$ is H or an alkyl or aryl group or a functionalized alkyl group or a functionalized aryl group.

8. The process of claim 6, wherein the donor substituents are alkyl or aryl groups, OR$^5$ or N(R$^5$)$_2$, wherein R$^5$ is H or an alkyl or aryl group or a functionalized alkyl group or a functionalized aryl group.

9. The process of claim 6, wherein the carbon-containing material is carbon black.

10. The process of claim 6, wherein the carbon-containing material is graphite powder, graphite fibers, carbon fibers, carbon fibrils, carbon nanotubes, carbon fabrics, glass-like carbon products, or active carbon.

11. The process of claim 6, wherein the organic compound represented by formula 1 is wherein R, R', R", R'", R"" are each, independently, H or an alkyl or aryl group with one or more acceptor or donor substituents or parts of a cyclic system with one or more acceptor or donor substituents and/or one or more hydrophilic or hydrophobic groups.

12. The process of claim 6, wherein the organic compound represented by formula 1 is
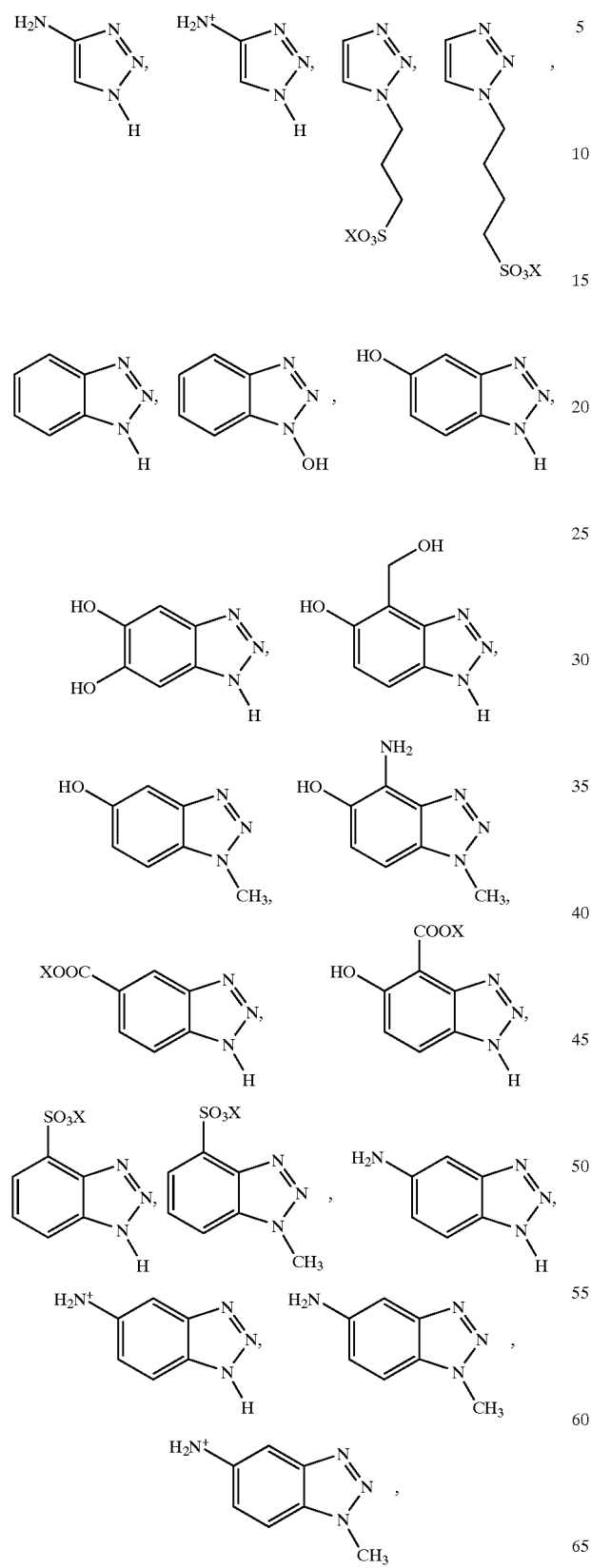
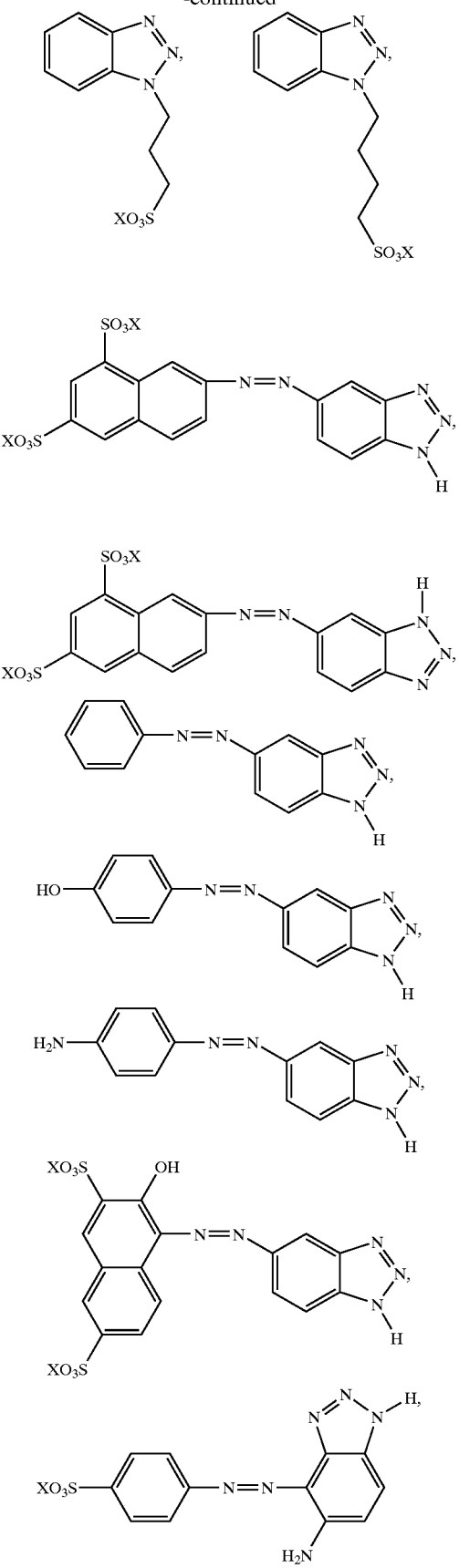

-continued

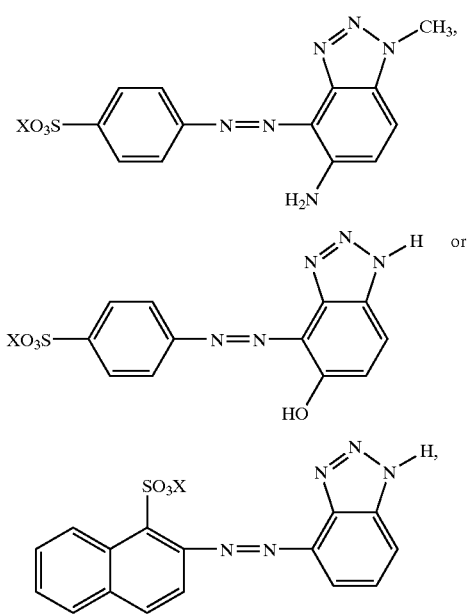

wherein
X is H, metal$^{n+}$, or N$^+$(R$^4$)$_4$,
n is 1, 2, or 3, and
R$^4$ is H or an alkyl or aryl group or a functionalized alkyl group or a functionalized aryl group.

13. A composition, comprising the carbon-containing material of claim 1 and at least one member selected from the group consisting of rubber, plastics, printing inks, inks, inkjet inks, lacquers, toners and colorants, bitumen, concrete, other constructional materials, and paper.

14. A method of making the composition of claim 13, comprising incorporating the carbon-containing material into a member selected from the group consisting of rubber, plastics, printing inks, inks, inkjet inks, lacquers, toners and colorants, bitumen, concrete, other constructional materials, and paper.

15. A dispersion, which contains the carbon-containing material with organic groups as claimed in claim 1.

16. An ink, lacquer, toner, or colorant that contains the dispersion of claim 15.

17. A method of making the ink, lacquer, toner or colorant of claim 16, comprising incorporating the dispersion of claim 15 into the ink, lacquer, toner, or colorant.

* * * * *